Nov. 19, 1963 H. B. LEWIS ETAL Plant Pat. 2,307
AZALEA PLANT
Filed Sept. 7, 1962 2 Sheets-Sheet 1
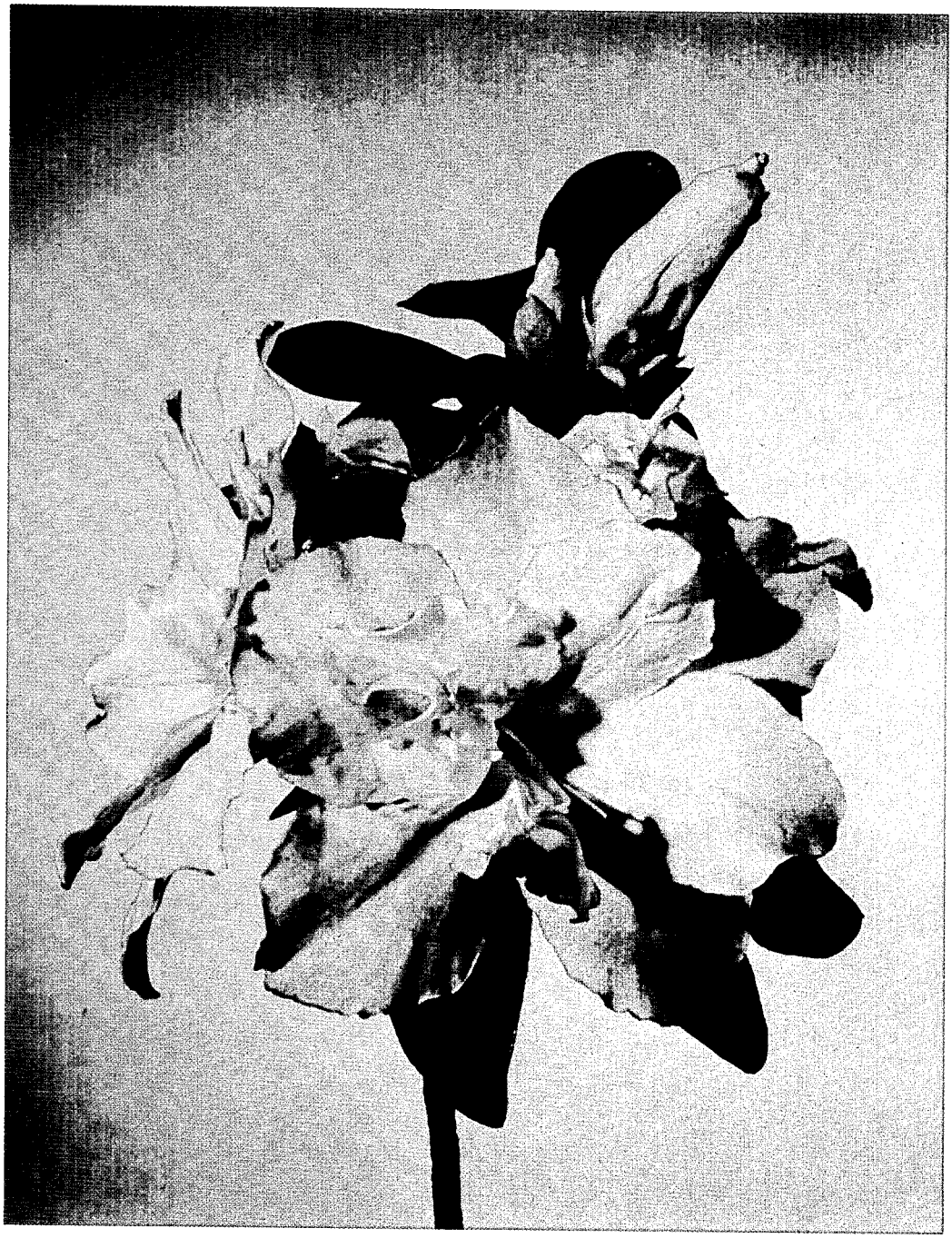
Inventors.
H. B. Lewis and
H. H. Lewis
By: Robb & Robb
Attorneys.

Nov. 19, 1963 H. B. LEWIS ETAL Plant Pat. 2,307
AZALEA PLANT
Filed Sept. 7, 1962 2 Sheets-Sheet 2
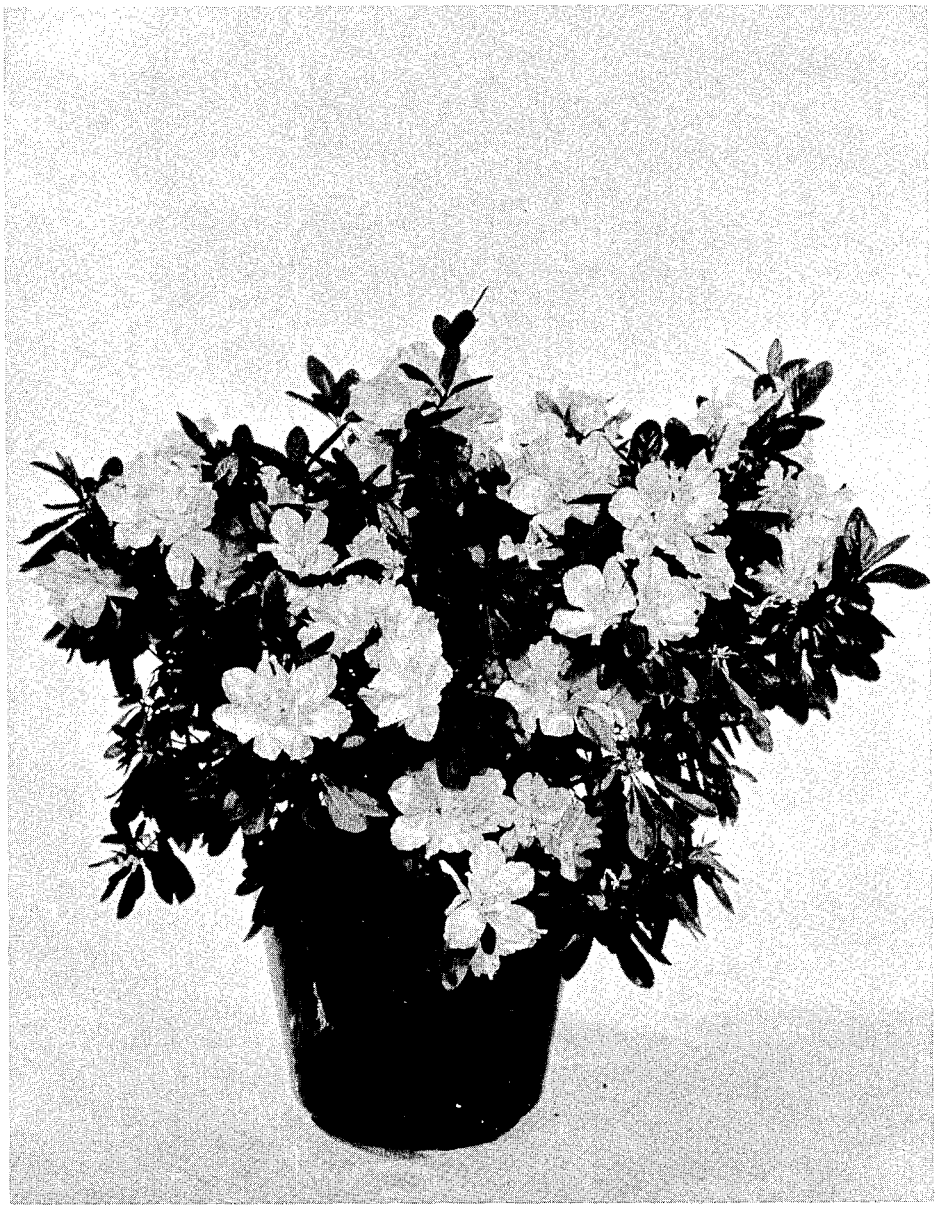
Inventors.
H. B. Lewis and
H. H. Lewis
By: Robb & Robb
Attorneys.

United States Patent Office

Plant Pat. 2,307
Patented Nov. 19, 1963

2,307
AZALEA PLANT

Hubert B. Lewis and Helen H. Lewis, both of 16562 E. Leffingwell Road, Whittier, Calif.

Filed Sept. 7, 1962, Ser. No. 222,249
1 Claim. (Cl. Plt.—56)

The present invention relates to a new and distinct variety of azalea plant which was originated by us by crossing the Belgian Indian variety known as "Pink Pearl" (unpatented) with the Rutherfordiana variety known as "L. J. Bobbink" (unpatented), the former being the seed parent and the latter being the pollen parent.

As the result of this breeding, we have produced a new azalea variety which is endowed with a new and improved combination of characteristics, as evidenced by the following features which are outstanding therein and which distinguish the new variety from its parents, as well as from all other varieties of which we are aware:

(1) Abundant foliage;

(2) A cluster habit of bloom; and (3) A distinctive and attractive Phlox Pink general color tonality of the flowers which resemble apple blossoms.

In comparison with its seed parent, the new variety does not resemble it in any way, but there is a slight resemblance to the pollen parent with respect to the vigor, flower shape and budding habit of the new variety.

Asexual reproduction of our new variety by cuttings, as performed at Rivera, California, and at Whittier, California, shows that the foregoing characteristics and distinctions come true to form and are established and transmitted through succeeding propagations.

The accompanying drawings show a typical specimen plant of our new azalea variety as depicted in black and white to illustrate its general form and habit of growth, as well as typical specimens of the flowers and foliage as depicted in color on a somewhat enlarged scale to better illustrate the details thereof.

The following is a detailed description of our new azalea variety, with color terminology in accordance with the Wilson Horticultural Color Chart, except where general color terms of ordinary dictionary significance are obvious:

Locality where grown and observed: Whittier, California.
Propagation: Holds its distinguishing characteristics through succeeding propagations by cuttings.

*Plant*

Form: Upright; much-branched.
Habit: Vigorous; upright; branching.
Rooting habit: Excellent.
Foliage:
*Size.*—Medium.
*Quantity.*—Abundant.

*Color.*—New foliage: upper side—Scheeles Green, Plate 860; under side—Scheeles Green, Plate 860/1. Old foliage: upper side—Spinach Green, Plate 0906; under side—Scheeles Green, Plate 860.
*Shape.*—Elongated; slightly cupped in mature leaves.
*Texture.*—Upper side—glossy; smooth. Under side—smooth; veined.
*Margin.*—Smooth edge.
*Aspect.*—Smooth; well-shaped.
*Disease resistance.*—Very good resistance to ordinary diseases to which azalea plants are normally subject, as determined by comparison with other varieties grown under the same cultural conditions at Whittier, California.

*Flowers*

Borne: 3 or 4 to stem; in clusters; on strong stems.
Blooming habit: An unusual habit of forming multiple branches at end of stems, with multiple buds, giving the appearance of a large ball of flowers when in bloom.
Blooming season: Spring; very good for forcing; may be forced from Christmas to Easter with proper pruning.
Quantity of bloom: Abundant, both outdoors and in greenhouse.
Continuity: One season. Lasting quality—very good.
Petalage: Under normal conditions, outer hose has 5 petals and inner hose has 4 or 5 petals, sometimes with a little center.
*Color.*—Outer petals ranging from Phlox Pink, Plate 625/1 to Phlox Pink, Plate 625/2, with some petals being Phlox Pink, Plate 625/3 and having a center line of Phlox Pink, Plate 625/1, resembling Apple Blossoms; center petals shade from Phlox Pink, Plate 625/2 at outer edge to Phlox Pink, Plate 625/3 at center, with dots on upper petals.
*Texture.*—Firm.
*Appearance.*—Inside—inside hose is offset from outer hose. Outside—outer petals range deeper in color.
*Shape.*—Ovate and oblong.
*Arrangement.*—Single to semi-double hose in hose.
Bud: Color—Phlox Pink, Plate 625.

*Reproductive Organs*

Stamens: 4 in number. Color—white.
Pollen: Color—white.
Style: Thin.
Ovaries: Normal.

We claim:

A new and distinct variety of azalea plant, substantially as herein shown and described, characterized particularly as to novelty by the unique combination of abundant foliage, a cluster habit of bloom, and a distinctive and attractive Phlox Pink general color tonality of the flowers which resemble apple blossoms.

No references cited.